US006152921A

United States Patent [19]

Gminder

[11] Patent Number: 6,152,921

[45] Date of Patent: Nov. 28, 2000

[54] HIGH FREQUENCY (HF) ELECTRODE FOR A HF INSTRUMENT OPERATING IN MONOPOLAR MODE

[75] Inventor: Frank Gminder, Trossingen, Germany

[73] Assignee: Karl Storz GmbH & Co. KG, Germany

[21] Appl. No.: 09/091,119

[22] PCT Filed: Dec. 23, 1996

[86] PCT No.: PCT/DE96/02471

§ 371 Date: Sep. 17, 1998

§ 102(e) Date: Sep. 17, 1998

[87] PCT Pub. No.: WO97/23168

PCT Pub. Date: Jul. 3, 1997

[30] Foreign Application Priority Data

Dec. 22, 1995 [DE] Germany ........................... 195 48 493

[51] Int. Cl.[7] ..................................................... A61B 18/18

[52] U.S. Cl. ................................................ 606/46; 600/49

[58] Field of Search ................................. 606/32, 41, 45, 606/46, 49, 50; 607/101

[56] References Cited

U.S. PATENT DOCUMENTS 5,549,605 8/1996 Hahnen ..................................... 606/46
5,569,244 10/1996 Hahnen ..................................... 606/46
5,582,610 12/1996 Grossi et al. ............................ 606/46
5,782,829 7/1998 Swiantek et al. ......................... 606/46

*Primary Examiner*—Linda C. M. Dvorak
*Assistant Examiner*—Roy Gibson
*Attorney, Agent, or Firm*—St. Onge Steward Johnston & Reens LLC

[57] ABSTRACT

Disclosed is a high-frequency electrode having an insulated lead extending in the direction of the longitudinal axis of a monopolar operating high-frequency instrument, and an electrode component, which is connected to the lead in an electrically conducting manner and with which the to be treated tissue is brought to engage, and which comprises two stirrups and a central section, characterized by the fact that said central section is designed like a plate having a longitudinal extension, i.e. an extension in the direction of the longitudinal axis of the instrument respectively the lead from 2 to 6 mm and that the stirrups are made of wire material having an essentially smaller longitudinal extension.

19 Claims, 2 Drawing Sheets

HIGH FREQUENCY (HF) ELECTRODE FOR A HF INSTRUMENT OPERATING IN MONOPOLAR MODE

TECHNICAL FIELD

The present invention relates to a high-frequency electrode for a monopolar operating high-frequency instrument according to the generic part of claim 1.

Electrodes of this type are utilized, for example, in HF-resectoscopes for the treatment of prostate adenomatous tissue.

STATE OF THE ART

With conventional loop-shaped electrodes comprising a thin wire with a diameter of typical up to 1 mm or a corresponding flat material, incision and surface coagulation effects utilized for stanching the blood of cut blood vessels occur depending on the type of current—cutting mode, coagulation mode, spray coagulation mode—of the employed high-frequency generator. In practice, a useable vaporization effect practically does not occur.

Furthermore, the kind of current influences the "processing result": dependent on the applied "current", in addition to the cutting effect, surface coagulation is generated which permits stanching the bleeding of blood vessels running near the surface.

Large area ball or roller electrodes to which "coagulation current" is applied usually are used only for large-area stanching of blood as the final step of the surgical procedure.

As an alternative for high-frequency tissue removal, lasers can be employed for tissue ablation. Lasers suited for this purpose are substantially more expensive than high-frequency generators, therefore attempts have been made to find ways to also be able to remove adinomatous tissue as bloodlessly as possible using high-frequency electrodes.

A number of authors have suggested using conventional monopolar electrodes with a cylindrical roll. Reference is made to U.S. Pat. No. 5,395,363, on which the wording of the generic part of claim 1 is based, only as an example.

The surface of the cylindrical roll can be designed in a variety of ways: rolls with smooth surfaces, with grooved surfaces or with pointed surfaces are known.

However, using high-frequency electrodes with rolls has the drawback that, for one the relatively large roll impedes the surgeon's vision. Secondly, it is only possible in practice to vaporize the tissue with such type rolls by supplying higher high-frequency power, efficiency being unsatisfactory. This means the patient is not only exposed to very high current flow respectively high energy, which involves high potential risk, for considerable time, but also the narcosis time is distinctly longer than in other surgical techniques.

DESCRIPTION OF THE INVENTION

The object of the present invention is to provide a high-frequency electrode for a monopolar-operating high-frequency instrument with which surgery time is shortened by vaporizing as well as cutting the tissue.

An invented solution to this object is described in claim 1. Further improvements of the present invention are the subject matter of claim 2 and the following claims.

An element of the present invention is that it was recognized that it is possible to vaporize as well as cut with an electrode, possessing basically the contour of a known loop, if this electrode is provided with a central section which has a longitudinal extension, i.e. an extension in the direction of the longitudinal axis of the lead respectively leads of at least 2 mm and not more than 6 mm. The stirrups joining the central section and the lead respectively leads, comprise in an as such known manner a wire material having a substantially smaller longitudinal extension, which according to claim 3 is not more than 1.5 mm preferably not more than 1 mm.

Conventional loops, on the other hand, are made of materials of the same dimensions, in particular of wire materials, with the longitudinal extension respectively the diameter of the wire being typically 1 mm.

The invented electrode permits simultaneous "bloodless" cutting and vaporizing of the tissue. On the basis of the inventive embodiment of the central section of the loop high-frequency current flows into the tissue in a large surface nonetheless confined manner and effects a coagulation and vaporization procedure during the cutting procedure! Nonetheless, it is still possible to "dig" respectively "excavate" to remove tissue with the invented electrode.

The selective application of the lateral stirrups having relatively small longitudinal extension permits using high-frequency electrodes designed according to the present invention having the advantages particular to conventional thin loop electrodes, notably removing respectively cutting off "parasol" sections of tissue.

It is preferred if the stirrups do not comprise a wire material having a round cross section, but according to claim 2 a band-shaped material respectively a material having an elliptical cross section, the longer axis of which extends in the direction of the longitudinal axis of the lead.

In the improvement described in claim 4, in which the lead, the stirrups and the central section are arranged in a kind of "Z" configuration, facilitates cleaning the cut-off tissue from the invented electrodes.

The improvement of the invented high-frequency electrodes having a sharpened cutting edge claimed in claim 9 permits optimized current flow from the cutting edge into the tissue upon incision. The high current density occurring at the edge leads to optimum incision into the tissue. Following incision, the electrode is held in such a manner that the current flows essentially perpendicular into the tissue from the "plate surface".

The ability to cut with the "rear" edge of the central section is supported by the central section having an elliptical longitudinal section (claim 10).

As the invented electrodes essentially has the general shape of a loop, it does not impede the surgeon's vision at the surgical site.

In another preferred embodiment described in claim 5, the central section in the transverse direction is shaped, in particular bent. In this way,large-surface application on the to-be-treated tissue is supported and simultaneously vision is not impeded, for example, by an endoscope utilized in a resectoscope.

The preferred width of the central section of at least (approximately) 3.5 mm and preferably of at least 4.5 mm results in particularly effective vaporization of the tissue during cutting (claim 6).

According to claim 8, it is advantageous if the central section is provided with grooves, because the grooves permit the "vapor" arising during vaporization to escape and optimize the ability of the current to enter the tissue.

The invented high-frequency electrode can be fabricated in an as such known manner and, in particular, can be made of high temperature resistant materials, in particular titanium alloys.

In another preferred embodiment, the top side of the central section is insulated in such a manner that current only flows through the bottom side of the central section, designed plate-shaped, thereby confining the current flow for vaporization and coagulation to the required region and reducing the patient's current load.

BRIEF DESCRIPTION OF THE DRAWING

The present invention is made more apparent in the following using a preferred embodiment with reference to the accompanying drawing, showing in.

DESCRIPTION OF PREFERRED EMBODIMENTS

Figure 1:
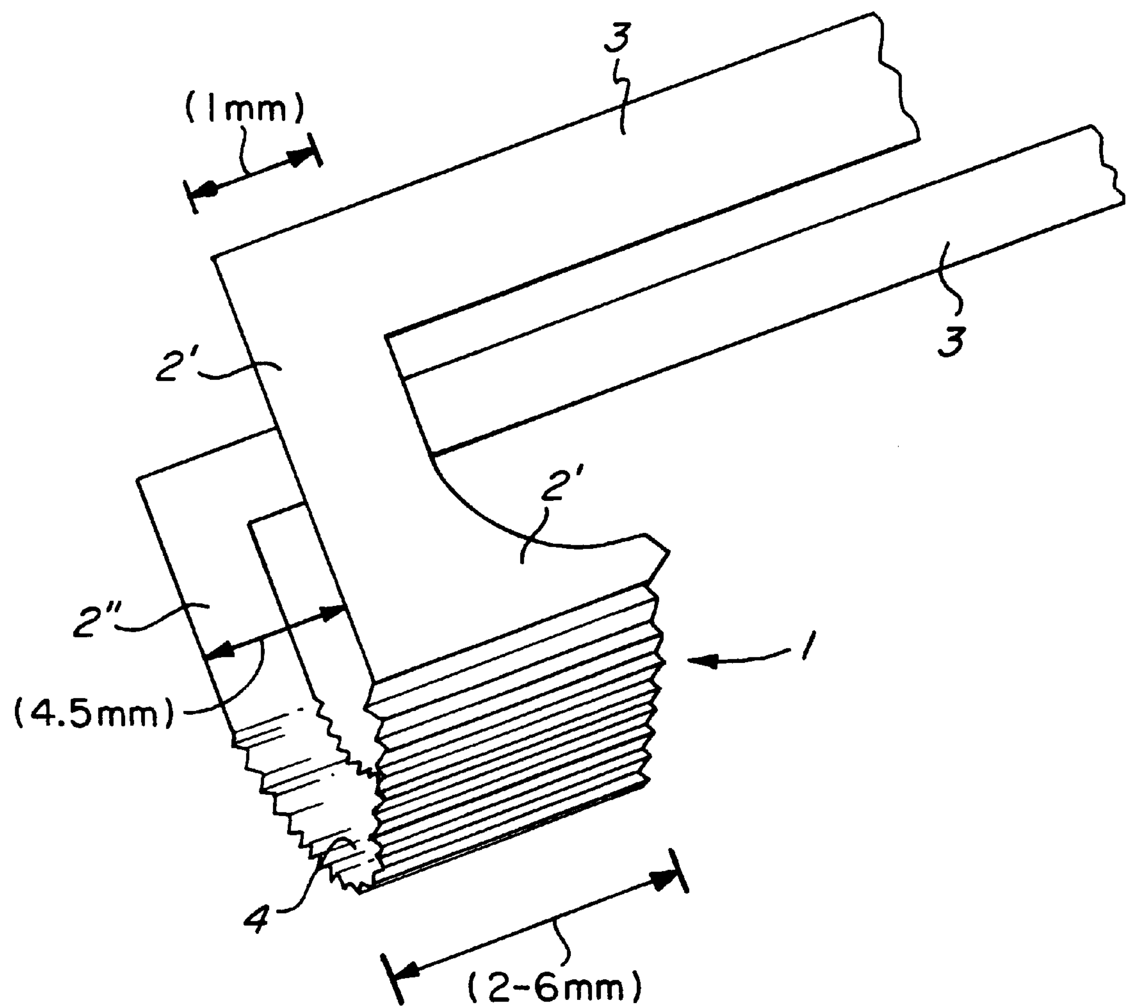
FIG. 1 an exploded diagram of an invented high-frequency electrode.

FIG. 1 shows a diagram of an invented high-frequency electrode. The electrode is provided with a central section 1 and two stirrups 2' respectively 2" joining the central section with an insulated lead 3, comprising in the depicted embodiment two rods. The high-frequency electrode is connected via the insulated lead 3, for example, to a standard resectoscope (not depicted), which is connected to a high-frequency generator, also not depicted. This high-frequency generator is preferably a regulated generator. Instruments respectively devices, such as those mass produced and sold by the applicant, Karl Storz GmbH & Co., Tuttlingen, Germany, can be used as resectoscopes and high-frequency generators.

The central section 1 of the invented high-frequency electrode has a longitudinal extension of 2 mm to 6 mm, preferably 3 to 5 mm. The width of the central section 1 is typically about 5 mm.

The stirrups are made of a wire material or a band-shaped material having a diameter respectively an extension in the direction of the longitudinal axis of the lead 3 of typically 1 mm, permitting in certain cases to also cut through the tissue with one of the stirrups.

Furthermore, the top side of the central section is provided with an insulation 4 and the bottom side with grooves.

By means of insulation 4, the current flow is limited in that the current only enters the tissue from the bottom side but not from the top side of the central section.

Figure 2A:
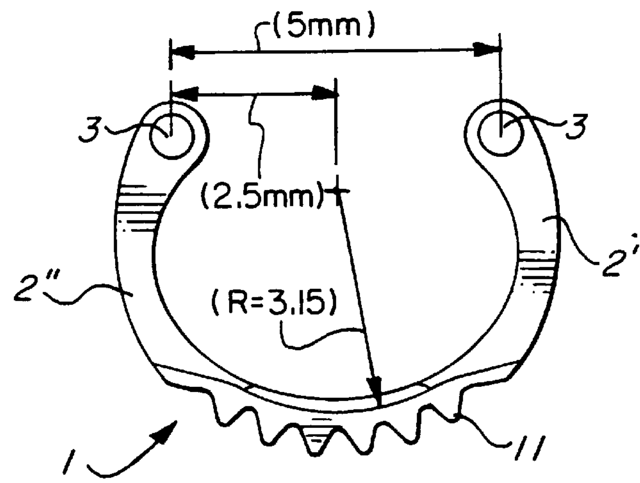
FIGS. 2*a* to *c* a practical preferred embodiment of an invented high-frequency electrode.
Figure 2C:
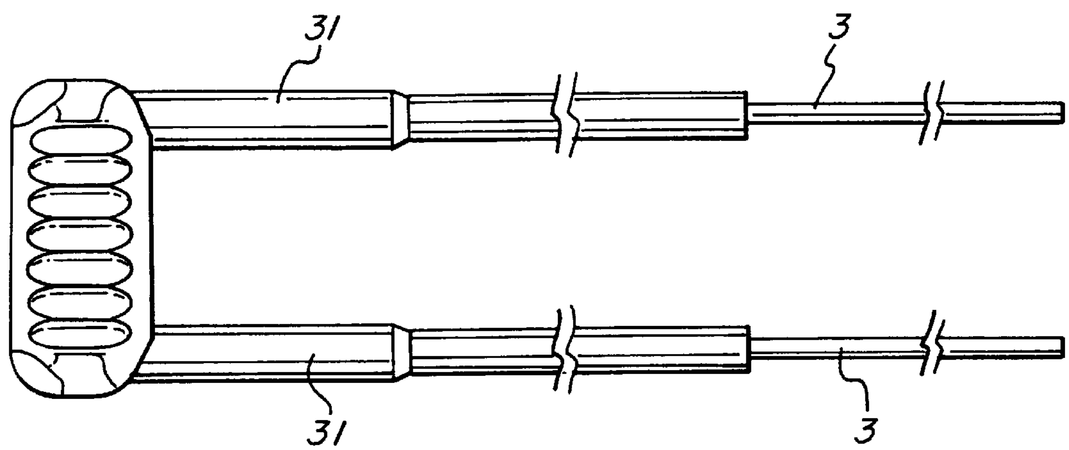
Figure 2B:
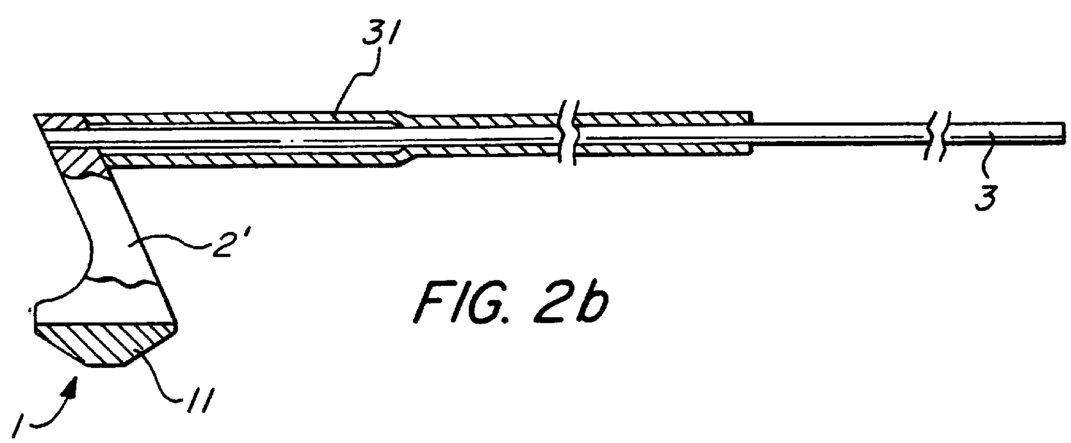

FIGS. 2*a* to 2*c* show in a front view (FIG. 2*a*), in a sectional view (from the side FIG. 2*b*) and a view from the bottom (FIG. 2*c*) a real embodiment of an invented electrode. Same respectively corresponding parts as in FIG. 1 are provided with the same reference numbers. In addition, the reference number 31 stands for an insulation of the leads and 11 for the grooves on the bottom side of the plate-shaped section 1.

FIGS. 2*a* and 2*b* show the particularly preferred dimensions. FIGS. 2*b* and 2*c* are executed using the same scale so that the other dimensions can be drawn from the figures.

The vaporization technique as well as the conventional cutting technique can be applied using the invented high-frequency electrode, thereby eliminating all the problems which can occur due to changing electrodes as required by the state of the art.

Furthermore, the very high current flow, thus a current flow involving potential risk can be selectively employed only when it is really required.

Simultaneous use of cutting and coagulation respectively vaporization methods makes the invented high-frequency electrode very efficient so that the narcosis times are distinctly shortened compared to other surgical methods.

What is claimed is:

1. A high-frequency electrode having:

an insulated lead extending in the direction of a longitudinal axis of a high-frequency instrument;

an electrode component connected to said lead in an electrically conducting manner, which comprises two stirrups;

and a central section characterized by the fact that said central section extends in the direction of the longitudinal axis about 2 to 6 mm from said lead and that said stirrups are made of material extending a smaller distance in the direction of the longitudinal axis than said central section; and said stirrups are made of a band-shaped material having an elliptical cross section.

2. An electrode according to claim 1, wherein said stirrups extend in the direction of the longitudinal axis not more than 1.5 mm.

3. An electrode according to claim 2, wherein said stirrups extend in the direction of the longitudinal axis about 1 mm.

4. An electrode according to claim 1, wherein said central section is shaped in a transverse direction with respect to the high-frequency instrument.

5. An electrode according to claim 2, wherein said central section has a width of at least 3.5 mm.

6. An electrode according to claim 5, wherein said central section has a width of at least 4.5 mm.

7. An electrode according to claim 2, wherein a bottom side of said central section is provided with grooves.

8. An electrode according to claim 1, wherein an edge of said central section facing a proximal region of the high-frequency instrument is shaped for cutting.

9. An electrode according to claim 1, wherein said central section has an approximately elliptical longitudinal section.

10. An electrode according to claim 1, wherein said electrode is made of titanium.

11. An electrode according to claim 1, wherein said central section extends in the direction of the longitudinal axis about 3 to 5 mm.

12. An electrode according to claim 1 wherein said lead, said stirrups and said central section are disposed in a "Z" shaped configuration.

13. An electrode according to claim 1 wherein a top side of said central section is provided with insulation.

14. An electrode according to claim 1 herein said lead, said stirrups and said central section are disposed in a "Z" shaped configuration and a top side of said central section is provided with insulation.

15. A high-frequency electrode having:

an insulated lead extending in the direction of a longitudinal axis of a high-frequency instrument;

an electrode component connected to said lead in an electrically conducting manner, which comprises two stirrups;

and a central section characterized by the fact that said central section extends in the direction fo the longitudinal axis about 2 to 6 mm from said lead and that said stirrups are made of material extending a smaller distance in the direction of the longitudinal axis than said central section; and said lead, said stirrups and said central section are disposed in a "Z" shaped configuration.

16. An electrode according to claim 15 wherein a top side of said central section is provided with insulation.

17. An electrode according to claim 15 wherein said central section has an approximately elliptical longitudinal section.

18. A high-frequency electrode having:

an insulated lead extending in the direction of a longitudinal axis of a high-frequency instrument;

an electrode component connected to said lead in an electrically conducting manner, which comprises two stirrups;

and a central section characterized by the fact that said central section extends in the direction of the longitudinal axis about 2 to 6 mm from said lead and that said stirrups are made of material extending a smaller distance in the direction of the longitudinal axis than said central section; and wherein a top side of said central section is provided with insulation.

19. An electrode according to claim 18 wherein said central section has an approximately elliptical longitudinal section.

* * * * *